(12) United States Patent
Mulvaney

(10) Patent No.: US 7,073,781 B2
(45) Date of Patent: Jul. 11, 2006

(54) HUMIDIFIER WITH ULTRAVIOLET GERMICIDIAL LIGHT

(75) Inventor: Patrick T. Mulvaney, Glen Allen, VA (US)

(73) Assignee: Hamilton Beach/Proctor-Silex, Inc., Glen Allen, VA (US)

( * ) Notice: Subject to any disclaimer, the term of this patent is extended or adjusted under 35 U.S.C. 154(b) by 554 days.

(21) Appl. No.: 10/188,783

(22) Filed: Jul. 3, 2002

(65) Prior Publication Data

US 2004/0005260 A1  Jan. 8, 2004

(51) Int. Cl.
*B01F 3/04* (2006.01)
*A61L 2/10* (2006.01)

(52) U.S. Cl. .................. 261/37; 422/124; 422/305; 422/186.3; 392/395; 392/403; 261/72.1; 239/34

(58) Field of Classification Search .................. 422/22, 422/24, 186.3, 305, 306; 392/395, 403, 405; 210/748; 261/37, DIG. 48, DIG. 46, 72.1; 251/37; 239/34
See application file for complete search history.

(56) References Cited

U.S. PATENT DOCUMENTS

| 2,265,252 | A |   | 12/1941 | Schaefer |   |
|---|---|---|---|---|---|
| 2,638,644 | A |   | 5/1953 | Rauhut |   |
| 3,812,370 | A |   | 5/1974 | LaViolette |   |
| 4,026,285 | A | * | 5/1977 | Jackson | ................ 128/200.17 |
| 4,362,090 | A |   | 12/1982 | Whiteley |   |
| 4,630,475 | A |   | 12/1986 | Mizoguchi |   |
| 4,899,057 | A |   | 2/1990 | Koji |   |
| 4,940,885 | A |   | 7/1990 | Challenger |   |
| 5,215,657 | A |   | 6/1993 | Goldfield et al. |   |
| 5,217,696 | A |   | 6/1993 | Wolverton et al. |   |
| 5,348,623 | A |   | 9/1994 | Salmon |   |
| 5,433,923 | A |   | 7/1995 | Wolverton et al. |   |
| 5,589,132 | A |   | 12/1996 | Zippel |   |
| 5,677,982 | A |   | 10/1997 | Levine et al. |   |
| 5,859,952 | A | * | 1/1999 | Levine et al. | ................ 392/405 |
| 6,042,720 | A |   | 3/2000 | Reber et al. |   |
| 6,098,963 | A | * | 8/2000 | Dubin et al. | .................. 261/66 |
| 6,117,219 | A |   | 9/2000 | Muhr |   |
| 6,845,971 | B1 | * | 1/2005 | Bachert | ....................... 261/37 |

FOREIGN PATENT DOCUMENTS

| EP | 0 446 011 A1 |   | 9/1991 |
|---|---|---|---|
| EP | 0 446 011 B1 |   | 9/1991 |
| JP | 2002104902 A | * | 4/2002 |

* cited by examiner

*Primary Examiner*—Krisanne Jastrzab
*Assistant Examiner*—Sean E. Conley
(74) *Attorney, Agent, or Firm*—Akin Gump Strauss Hauer & Feld, LLP

(57) ABSTRACT

A humidifier which includes a reservoir of water in fluid communication with an evaporation chamber. Some of the water that enters the evaporation chamber vaporizes and enters the ambient environment. A remainder of the water does not evaporate and flows into a collection container in fluid communication with the reservoir. The unevaporated water is then exposed to a source of ultraviolet radiation which helps to inhibit the ability of various organisms contained therein to reproduce in the future. After irradiation, the unevaporated water travels from the collection container to the reservoir.

9 Claims, 2 Drawing Sheets

HUMIDIFIER WITH ULTRAVIOLET GERMICIDIAL LIGHT

BACKGROUND OF THE INVENTION

The present invention relates to humidifiers and, more particularly, to a humidifier with a source of ultraviolet light for sterilizing water that passes through the humidifier without being humidified.

Various humidification systems are known and have previously been described in the prior art. However, none of these humidifiers are self-cleaning. Thus, mold spores in air and viruses on dust particles plate out on evaporative devices such as a wick, but are not continuously washed away and irradiated. Therefore, it is not possible to remove accumulated articulate matter from these previous humidifiers without interrupting their operation.

FIG. 1 shows a schematic representation of a typical prior art humidification system. FIG. 2 illustrates a block diagram of the prior art humidifier represented in FIG. 1. Water 100 flows from a storage tank 102 into a reservoir 104 through a conduit 106. The water 100 then enters an ultraviolet radiation chamber 108 having a source of ultra violet light 109. The ultraviolet radiation affects certain organisms such that the ability of such organisms to reproduce is inhibited. Irradiated water then enters an evaporation chamber 110, where some of it evaporates and enters the ambient air as water vapor 112. The internal mechanism of the evaporation chamber 110 collects a steadily increasing quantity of air borne particles. There is no continuous process for removing these particles and allowing more efficient operation of the humidifier.

Another known humidifier has a base and a removably mounted water reservoir or container. Water flows from a compartment in the base, through a hole in a partition and into a sterilization chamber. An ultraviolet lamp is positioned beside the sterilization chamber. Ultraviolet light passes from the ultraviolet light to the sterilization chamber through a transparent window. Irradiated water then flows through an opening in a second partition and into a third chamber, where it is delivered to a heating chamber. Various means can be utilized to increase system humidity including a wick or other large surface-area evaporator. Particles are allowed to accumulate in the heating chamber without being washed away. Thus, the evaporative efficiency of the humidifying system is steadily reduced. Large quantities of water must be continuously added to the system to attain significant levels of humidification. In addition, some of the collected foreign substances routinely travel with the evaporated water into ambient air, an undesirable effect. The humidifier of the present invention effectively avoids these problems.

BRIEF SUMMARY OF THE INVENTION

Briefly stated, the present invention is directed to an apparatus for humidifying air in rooms. The apparatus includes a reservoir containing water. An evaporation chamber is in fluid communication with the reservoir and receives water from the reservoir. A first portion of the water in the evaporation chamber evaporates and becomes water vapor, which travels into ambient air. A remaining portion of the water in the evaporation chamber does not evaporate and flows into a collection container in fluid communication with the reservoir such that the remaining portion of the water flows from the collection container to the reservoir. A source of ultraviolet radiation irradiates the remaining portion of the water before the remaining portion of the water returns to the reservoir, inhibiting the ability of various micro-organisms, such as bacteria and viruses, and other organisms which are present in the water to reproduce at a later time.

BRIEF DESCRIPTION OF THE SEVERAL VIEWS OF THE DRAWINGS

The foregoing summary, as well as the following detailed description of the preferred embodiment of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
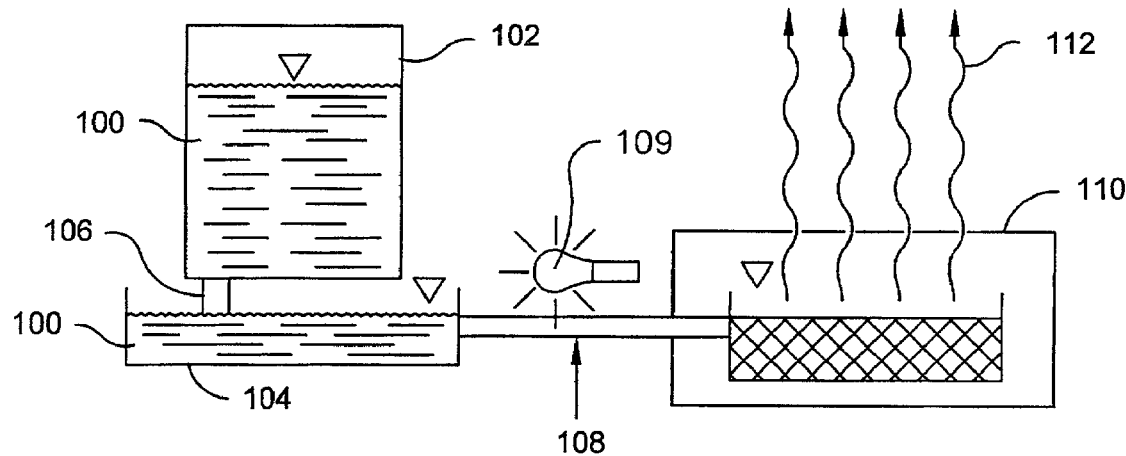
FIG. 1 is a schematic diagram of a conventional humidifier.

Certain terminology is used in the following description for convenience only and is not limiting. The words "right", "left", "lower" and "upper" designate directions in the drawings to which reference is made. The words "inwardly" and "outwardly" refer to directions toward and away from, respectively, the geometric center of the humidifier and designated parts thereof. The terminology includes the words above specifically mentioned, derivatives thereof and words of similar import.

Figure 3:
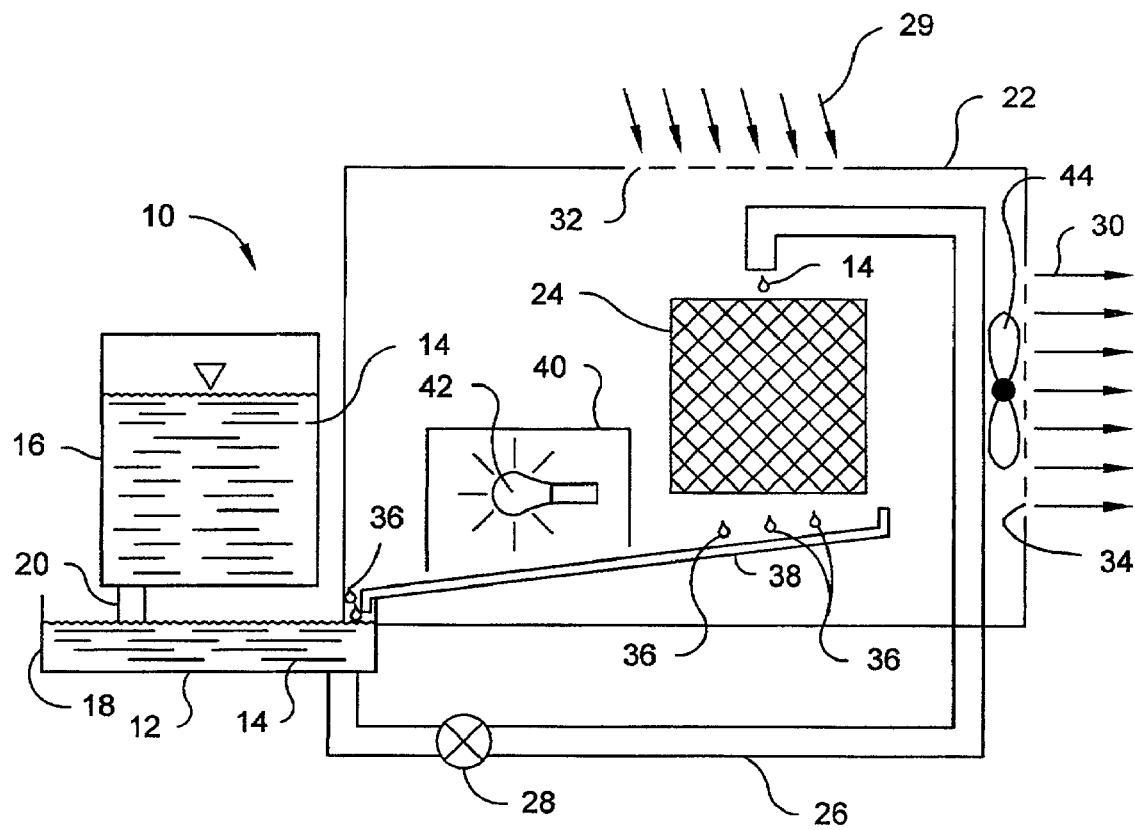
FIG. 3 is a schematic diagram of a humidifier in accordance with a first preferred embodiment of the invention.
Figure 2:
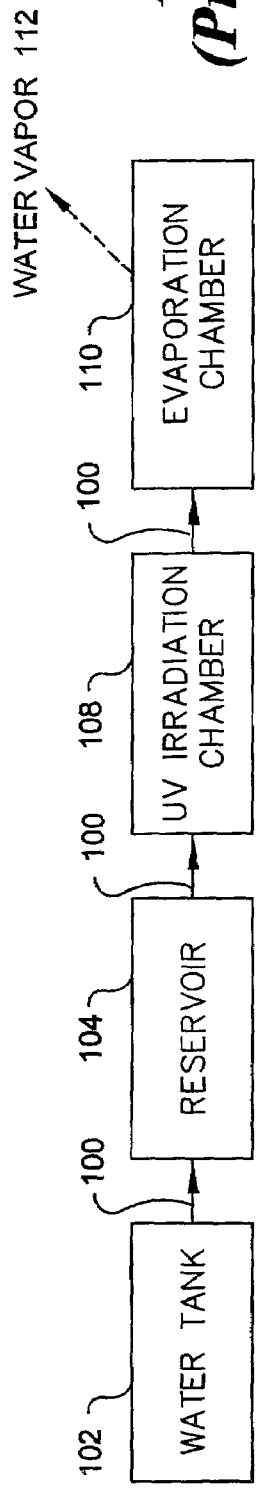
FIG. 2 is a block diagram of the conventional humidifier shown in FIG. 1.
Figure 4:
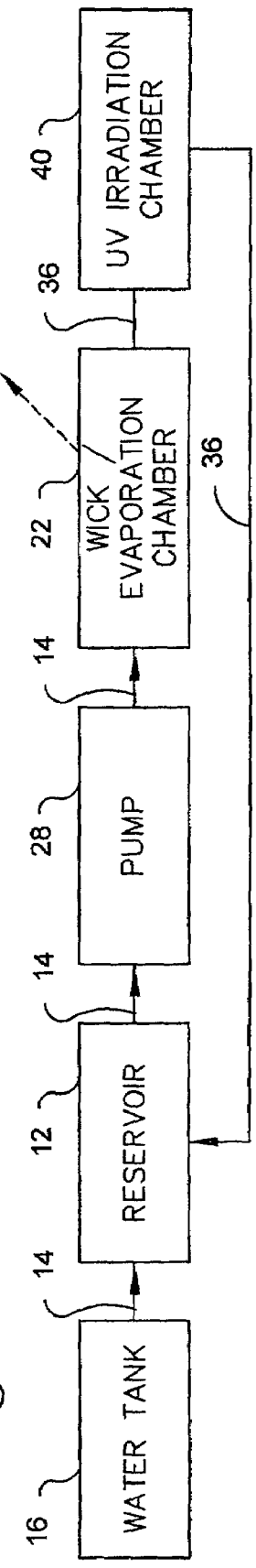
FIG. 4 is a block diagram of the humidifier shown in FIG. 3.

Referring now to the drawings in detail, wherein like numerals are used to indicate like elements throughout, there is shown in FIGS. 3 and 4 a first preferred embodiment of a humidifier, generally designated 10, for humidifying air in rooms (not shown). The humidifier 10 includes a reservoir 12 containing water 14. In the preferred embodiment, the reservoir 12 includes a tank 16 in fluid communication with a tray 18 via a conduit 20. The reservoir 12 is substantially open to the atmosphere, meaning that the reservoir 12 is part of an open fluid system, as opposed to a closed fluid system. The tank 16 includes a supply of water 14 which is fed to the tray 18 via a standard gravity fed system, which is well understood by those of ordinary skill in the art. As mentioned above, the reservoir 12 is shown schematically in FIG. 3. The details of the reservoir 12, tank 16, gravity feed system and tray 18 are not pertinent to the present invention as they could be constructed of any well known system understood by those of ordinary skill in the art and, therefore, are not described in detail for purposes of convenience only and is not limiting.

The humidifier 10 includes an evaporation chamber 22 in fluid communication with the reservoir 12, thereby receiving water 14 from the reservoir 12. Positioned within the evaporation chamber 22 is an evaporative device 24, such as a wick or evaporative pad (schematically shown). However, it is understood by those of ordinary skill in the art from this disclosure that the precise evaporative system within the evaporation chamber 22 is not pertinent to the present invention and could comprise other types of evaporation mechanisms or devices. The water 14 flows from the reservoir 12 to the evaporation chamber 22 via a piping network 26. The piping network 26 has at least one mechanical pump 28. In the preferred embodiment, the piping network 26 can be any of a plurality of conduits or other fluid passages which deliver the water 14 from the reservoir 12 directly to the evaporation chamber 22. Piping networks for this purpose are well known to those of ordinary skill in the art and, therefore, details of the piping network 26 have been omitted for purposes of convenience only and are not limiting.

The pump 28 urges the water 14 through the piping network 26, releasing the water 14 onto the evaporative device 24 within the evaporation chamber 22. Unhumidified air 29 is drawn into the evaporation chamber 22 through at least one inlet 32. Although the at least one inlet 32 is portrayed in FIG. 1 as being through the top of the evaporation chamber 22, it is within the spirit and scope of the present invention that the inlet 32 be through any of the sides (including the top and the bottom) of the evaporation chamber 22 or through any combination of the sides.

Once within the evaporation chamber 22, the unhumidified air 29 moves across or through the evaporative device 24 causing a first portion of the water 14 to evaporate into water vapor. The unhumidified air 29 then picks up the water vapor that has evaporated from the first portion of water 14 within the evaporative device 24 and becomes humidified air 30. The humidified air 30 is then urged out of the evaporation chamber 22 through at least one outlet 34. Although the at least one outlet 34 is portrayed in FIG. 1 as being through the right side of the evaporation chamber 22, it is within the spirit and scope of the present invention that the outlet 34 be through any of the sides (including the top and the bottom) of the evaporation chamber 22 or through any combination of the sides, the only requirement being that the at least one outlet 34 be spaced from the at least one inlet 32 such that a path of the air through the evaporation chamber 22 leads through or across the evaporative device 24. The unhumidified air 29 is drawn into, moved through, and forced out of the evaporation chamber 22 using a fan 44 or any other means (not shown) to move air.

A remaining portion 36 of the water 14 that has not evaporated remains within and passes through the evaporative device 24, dripping from the bottom of the evaporative device 24. That is, evaporative devices are not 100% efficient in that not all of the water passing therethrough evaporates. Conventionally, the unevaporated water returns to the reservoir where it is recycled. In the present invention, the remaining portion 36 of the water 14 exits the evaporative device 22 and flows into a collection container 38, which is in fluid communication with the reservoir 12. The precise structure of the at least one inlet 32, the at least one outlet 34, and the evaporation chamber 22 could be easily derived by one of ordinary skill in the art from this disclosure and are schematically shown for convenience only.

The collection container 38 is portrayed in the form of a tray positioned beneath the evaporative device 24 to collect the remaining portion 36 of the water 14. The collection container 38 funnels the remaining portion 36 of the water 14 into the reservoir 12. The collection container 38 can be of any configuration known to those of ordinary skill in the art which will collect the remaining portion 36 of the water 14 and convey it back to the reservoir 12, including, but not limited to, a planar system in which there is a distinct one-way flow path that allows water to re-enter the reservoir 12 from the evaporation chamber 22 and prevents the reverse movement.

A source of ultraviolet radiation within an ultraviolet radiation chamber 40 irradiates the remaining portion 36 of the water 14 before the remaining portion 36 of the water 14 returns to the reservoir 12, helping to inhibit the ability of various micro-organisms, such as bacteria and viruses, and other organisms which are present in the remaining portion 36 of the water 14 to reproduce in the future. The source of ultraviolet radiation is preferably in the form of an ultraviolet light 42 which is positioned to direct emitted light into the remaining portion 36 of the water 14 as it flows back to the reservoir 12. Although the source of ultraviolet radiation of the present invention is the ultraviolet light 42, it is within the spirit and scope of the invention that the source of ultraviolet radiation be any ultraviolet radiation-emitting device. The specific design of the ultraviolet radiation system is not pertinent to the present invention and is known to those of ordinary skill in the art, and therefore, further description thereof is omitted for purposes of convenience only and is not limiting.

As mentioned above, after being irradiated, the remaining portion 36 of the water 14 flows from the collection container 38 into the reservoir 12. Therefore, a continuous flow of water 14 is realized within the humidifier 10. The continuous flow of water 14 allows constant movement of water 14 through the evaporative device 24, effectively flushing from the evaporative device 24 a majority of the contaminants that are caught within the evaporative device 24 during the evaporation of the water 14. The organisms flushed from the evaporative device 24 are then irradiated, helping to inhibit their ability to reproduce. In this way, the humidifier 10 of the present invention is self-cleaning, reducing the amount of harmful contaminants in the humidified air 30 and the water 14 and lengthening the life of the evaporative devices 24 by lessening the amount of contaminants that remain within it.

Additional features affecting the operation of the humidifier can also be provided. Typically, a control system, which can be computer based (not shown) can regulate the pump 28 and the fan 44 for dispersing the humidified air 30. The operation of the pump 28 regulates the flow rate of the water 14 through the humidifier 10, and the operation of the fan 44 regulates the rate of evaporation of the water 14 from the evaporative device 24 as a function of the particular environmental conditions at the time of operation. The control system can function based on the principles of level-control, flow-control, or a combination of both. A level-control system would monitor the level of water 14 in the tank 16 and use this data to automatically open and close the valve as warranted. A flow-control system would monitor the flow of water 14 through the piping network 26 and use this data to automatically open and close the valve as warranted. The humidifier 10 preferably receives a reliable source of alternating current, such as from an electrical outlet, for powering the humidifier 10 in a manner well understood by those of ordinary skill in the art.

Although the evaporation chamber 22 of the present invention is portrayed as surrounding the evaporative device 24, the radiation chamber 40, the collection container 38, and a portion of the piping 26, it is within the spirit and scope of the present invention that the evaporation chamber 22 contain the evaporative device 24 and any combination of or none of the remaining components of the humidifier 10.

The humidifier 10 operates in a continuous manner. The pump 28 increases the pressure of the water 14 as it travels through the piping network 26 into the evaporation chamber 22, where the first portion of the water 14 becomes water vapor 30. The remaining portion 36 of the water 14 flows from the evaporative device 24 and into the collection container 38, through the ultraviolet radiation chamber 40, and into the reservoir 12, where the water 14 is then recycled.

Figure 5:
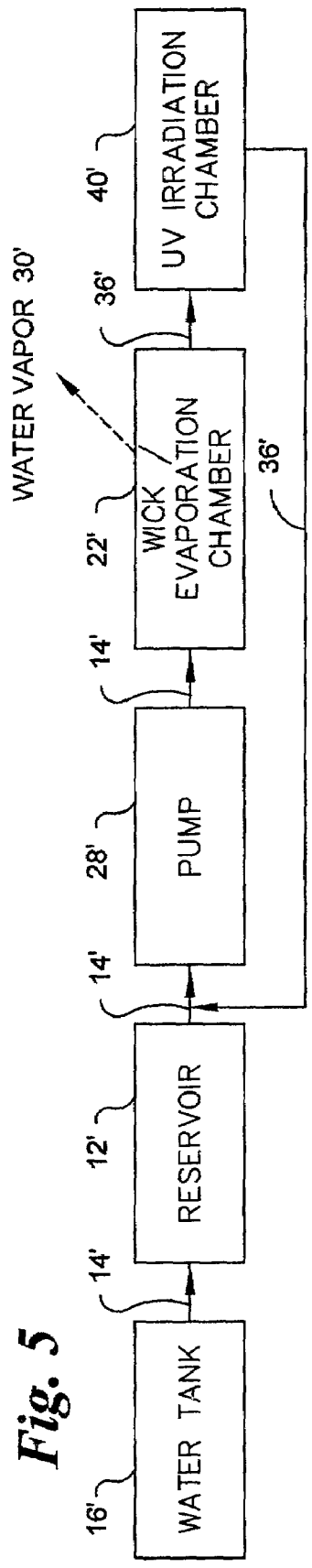
FIG. 5 is a block diagram of a humidifier in accordance with a second preferred embodiment of the invention.

The second preferred embodiment of the present invention is illustrated in the block diagram shown in FIG. 5, wherein like reference numerals which correspond to the first embodiment shown in FIGS. 3 and 4 are designated with the prime symbol. The first and second preferred embodiments are similar. Accordingly, only the differences between the two embodiments are set forth below. The remaining portion 36' of the water 14' is similarly exposed to the source of ultraviolet radiation within an ultraviolet chamber 40', inhibiting the ability of various organisms to reproduce in the future. However, the remaining portion 36' of the water 14', after irradiation, is fed to the piping network at a location just before the pump 28'. Otherwise, the second preferred embodiment of the invention operates in essentially the same manner as the first preferred embodiment illustrated in FIGS. 3 and 4.

It will be appreciated by those skilled in the art that changes could be made to the embodiments described above without departing from the broad inventive concept thereof. It will be understood, therefore, that this invention is not limited to the particular embodiments disclosed, but it is intended to cover modifications within the spirit and scope of the present invention as defined by the appended claims.

What is claimed is:

1. An apparatus for humidifying air in rooms, the apparatus comprising:
    a reservoir containing water;
    an evaporation chamber in fluid communication with the reservoir and receiving water from the reservoir, a first portion of the water in the evaporation chamber evaporates and becomes water vapor, which travels into ambient air, and a remaining portion of the water in the evaporation chamber does not evaporate and flows into a collection container in fluid communication with the reservoir such that the remaining portion of the water flows from the collection container to the reservoir;
    at least one of a wick and an evaporative pad in the evaporative chamber which receives at least a portion of the water;
    a fan that forces ambient air through the evaporation chamber to regulate a rate of evaporation of the water from the at least one of the wick and the evaporative pad; and
    a source of ultraviolet radiation which irradiates the remaining portion of the water before the remaining portion of the water returns to the reservoir, helping to inhibit the ability of various micro-organisms, such as bacteria and viruses, and other organisms which are present in the remaining portion of the water to subsequently reproduce.

2. The apparatus of claim 1, wherein the reservoir is substantially open to the atmosphere.

3. The apparatus of claim 1 further comprising:
    a piping network wherein the water flows from the reservoir to the evaporation chamber through the piping network.

4. The apparatus of claim 3, wherein the piping network has at least one mechanical pump.

5. The apparatus of claim 1, wherein the evaporation chamber contains at least one air inlet and at least one air outlet.

6. The apparatus of claim 5, wherein the ambient air enters the evaporation chamber through the at least one air inlet, which is located in a top of the evaporation chamber.

7. The apparatus of claim 5, wherein the water vapor generally exits the evaporation chamber through the at least one air outlet, which is located in a side of the evaporation chamber.

8. The apparatus of claim 1, wherein the evaporation chamber contains at least one opening.

9. An apparatus for humidifying air in rooms, the apparatus comprising:
    a reservoir containing water;
    a piping network for transporting the water from the reservoir into an evaporation chamber;
    the evaporation chamber being in fluid communication with the reservoir and receiving water from the reservoir, a first portion of the water in the evaporation chamber evaporates and becomes water vapor, which travels into ambient air, and a remaining portion of the water in the evaporation chamber does not evaporate and flows directly into a collection container and then directly re-enters the piping network;
    at least one of a wick and an evaporative pad in the evaporative chamber which receives at least a portion of the water;
    a fan that forces ambient air through the evaporation chamber to regulate a rate of evaporation of the water from the at least one of the wick and the evaporative pad; and
    a source of ultraviolet radiation which irradiates the remaining portion of the water before the remaining portion of the water re-enters the piping network, helping to inhibit the ability of various micro-organisms, such as bacteria and viruses, and other organisms which are present in the remaining portion of the water to subsequently reproduce.

\* \* \* \* \*